United States Patent [19]

Freed, deceased et al.

[11] 4,349,674
[45] Sep. 14, 1982

[54] QUINOALINYL ESTERS OF CARBAMIMIDOTHIOIC ACIDS

[75] Inventors: Elisabeth H. Freed, deceased, late of Paoli, Pa., by Meier E. Freed, executor; Peter H. L. Wei, Springfield; Ronald J. McCaully, Malvern, both of Pa.

[73] Assignee: American Home Products Corporation, New York, N.Y.

[21] Appl. No.: 970,295

[22] Filed: Dec. 18, 1978

[51] Int. Cl.³ .................. C07D 241/42; C07D 401/12; A61K 31/495

[52] U.S. Cl. ........................... 544/353; 544/554; 260/243.3; 424/250

[58] Field of Search .................. 260/243.3; 544/353, 544/354; 424/250

[56] References Cited

U.S. PATENT DOCUMENTS 3,040,046  6/1962  Sasse et al. ..................... 544/354
3,415,828  10/1968  Sasse et al. ..................... 544/354
3,472,848  10/1969  Cragoe et al. ................... 544/354

OTHER PUBLICATIONS

Wolf et al., J. Am. Chem. Soc., 76, p. 2266, (1954).

Primary Examiner—David B. Springer
Attorney, Agent, or Firm—Arthur G. Seifert

[57] ABSTRACT

The compounds of this invention are designated as quinoxalinyl esters of carbamimidothioic acids and exhibit the pharmacological properties of preventing gastric ulcers, reducing gastric secretions and lowering blood pressure. The compounds have the following structural formula:

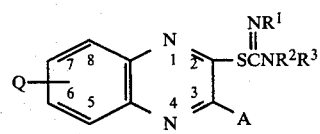

in which

Q is hydrogen or nitro;

A is hydrogen, methyl, ethyl, propyl, isopropyl, n-butyl, carbomethoxy, carbethoxy, carbopropoxy, carbisopropoxy, carbobutoxy, carbisobutoxy, or carbo-t-butoxy; and $R^1$, $R^2$, and $R^3$ are, independently, hydrogen, methyl, ethyl, propyl, isopropyl, n-butyl, isobutyl, t-butyl, allyl, or $R^1$ and $R^3$ may be concatenated with a carbon chain having 4 carbon atoms with $R^2$ then being hydrogen; except that, when A and Q are hydrogen, $R^1$, $R^2$, and $R^3$ may not all be hydrogen; and with the further exception that, where A is methyl and $R^1$, $R^2$, and Q are all hydrogen, $R^3$ may not be ethyl;

or a pharmaceutically acceptable salt thereof.

23 Claims, No Drawings

QUINOALINYL ESTERS OF CARBAMIMIDOTHIOIC ACIDS

SUMMARY OF THE INVENTION

The compounds of this invention are designated as quinoxalinyl esters of carbamimidothioic acids and exhibit the pharmacological properties of preventing gastric ulcers, reducing gastric secretions, and lowering blood pressure. The compounds have the following structural formulae:

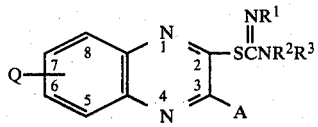

in which
Q is hydrogen or nitro;
A is hydrogen, methyl, ethyl, propyl, isopropyl, n-butyl, carbomethoxy, carbethoxy, carbopropoxy, carbisopropoxy, carbobutoxy, carbisobutoxy, or carbo-t-butoxy; and
$R^1$, $R^2$ and $R^3$ are, independently, hydrogen, methyl, ethyl, propyl, isopropyl, n-butyl, isobutyl, t-butyl, allyl, or $R^1$ and $R^3$ may be concatenated with a carbon chain having four carbon atoms with $R^2$ then being hydrogen; except that, when A and Q are hydrogen, $R^1$, $R^2$, and $R^3$ may not all be hydrogen; and with the further exception that, where A is methyl and $R^1$, $R^2$ and Q are all hydrogen, $R^3$ may not be ethyl; or a pharmaceutically acceptable salt thereof.

One group of preferred compounds of the invention are those in which Q, A, and $R^2$ are each hydrogen.

Another preferred group of compounds of the invention are those in which Q and $R^2$ are each hydrogen. Most preferred are such compounds in which A is methyl or carbethoxy.

Preferred combinations of $R^1$ and $R^3$ are both hydrogen; both methyl; both ethyl; both propyl; both isopropyl; both butyl; both allyl; $R^1$ is hydrogen and $R^3$ is methyl; $R^1$ is hydrogen and $R^3$ is butyl; $R^1$ is hydrogen and $R^3$ is allyl; and $R^1$ and $R^3$ are concatenated with a four carbon atom chain. In each such combination the most preferred compounds are those in which $R^2$ is hydrogen.

The quinoxaline ring numbering system shown in Formula I is used throughout this disclosure. Accordingly, all compounds of this invention are named with the thiourea moiety at the 2-position of the quinoxaline ring and with the alkyl or carbalkoxy substituent at the 3-position thereof. In addition, the carbalkoxy compounds of the invention are named as carboxylic acid esters.

Another group of preferred compounds of the invention are those in which Q is nitro and A is lower alkyl (except isobutyl or t-butyl). Particularly preferred are such compounds in which Q is 6-nitro and A is methyl.

As used herein the term "butyl" refers to n-butyl and the term "propyl" refers to n-propyl. Also the term "lower alkyl" refers to aliphatic hydrocarbon groups having from one to four carbon atoms.

It should be understood that those compounds in which one of $R^1$, $R^2$, and $R^3$ is a lower alkyl group or an allyl group and the other two are hydrogen may exist as tautomers and applicants' invention embraces such tautomers as the full equivalent of the named compound. Additionally, applicants' invention embraces a mixture of the tautomers as the full equivalent of the named compound. Examples of such tautomeric products are those produced in the working examples numbers 6, 7, and 11.

Detailed Description
BACKGROUND OF THE INVENTION

U.S. Pat. No. 3,260,726 (1966) discloses various heterocyclic thioureas with aryl substituents on the imido nitrogen of the thiourea moiety, which are disclosed as herbicides. Example 4 of said patent shows the preparation of (N,N-dimethyl-N'-phenyl)carbamimidothioic acid (3-methyl-2-quinoxalinyl)ester.

Wolf et al. discloses the preparation of unsubstituted S-2-quinoxalyl-isothiouronium chloride [carbamimidothioic acid (2-quinoxalinyl)ester, hydrochloride] in J. Am. Chem. Soc., 76, 2266 (1954). This compound was prepared by Wolf et al. as an intermediate in the preparation of quinoxaline-2-thiol.

The quinoxaline esters of carbamimidothioic acid of the present invention, on the other hand, are variously substituted with alkyl substituents on one or both nitrogens of the thiourea moiety, or with nitro, alkyl or carbalkoxy substituents on the quinoxaline ring, or with a combination of such substitutions. Additionally, the compound of the present invention exhibit the pharmacological properties of preventing gastric ulcers, reducing gastric secretions, and lowering blood pressure.

PHARMACOLOGICAL ACTIVITY

The anti-ulcer activity of the compounds of the invention may be demonstrated by means of the cold-restraint procedure, a standard test for anti-ulcer activity. In this test the anti-ulcer activity of a compound is the determination of the affect the subject compound has on animals inflicted with gastric ulcers caused by cold-restraint stress conditions according to the modification of the procedure of Brodie and Hanson, J. Appl. Physiol., 15, 291–294 (1960). In this test procedure the subject male Charles River rats, weighing between 120–160 gm., are deprived of food for 18 hr. with water ad lib. The rats are divided into groups of ten and dosed by the oral route with test compound, 50 mg/kg., or vehicle control, 0.5% carboxymethylcellulose, in a volume of 5 ml/kg. Immediately after dosing the animals are inserted into aluminum restraining tubes measuring 1⅝ inches in diameter by 8 inches and placed in the cold (4°±1° C.). The time in the cold is adjusted so that 90% of the control animals exhibit ulcers. At the end of the test period the animals are killed, the duodenum and esophagus ligated, and the stomach removed. The stomachs are inflated with water, opened along the lesser curvature, spread over the index finger, and the mucosa wiped off to expose the submucosa. The number of hemorrhage sites in the submucosa are counted by visual observation and recorded; however, since these numbers are so variable, only the incidence of ulcer (i.e., the number of rats with ulcers) are used for evaluation.

Activity is determined by calculating a percent inhibition which is calculated as follows:

$$\frac{\% \text{ rats with ulcers in control} - \% \text{ rats with ulcers in treatment} \times 100}{\% \text{ rats with ulcers in control}} = \% \text{ inhibition}$$

Compounds eliciting a greater than 70% inhibition are significantly different from the control group using a corrected Chi square analysis.

When administered according to the above-described procedure in doses of 5–100 mg/kg. (milligrams per kilograms of body weight), the compounds of the invention, except 2-aminoiminomethylthio-3-quinoxalinecarboxylic acid ethyl ester, exhibit ulcer inhibiting properties.

A number of standard pharmacological tests may also be employed to demonstrate the effectiveness of the compounds of the invention in inhibiting gastric secretions. Such anti-secretory activity is also evidence of anti-ulcer activity. One such test is a modification of the method of Shay et al., Gastroenterology, 26, 906-913 (1954). In this procedure male Charles River rats weighing 200–300 grams are deprived of food but not water for 24 hours prior to use. Water is, however, withheld during the experiment. The rats are weighed, anesthetized with ether and the pylorus ligated according to the method of Shay et al. Treatment or vehicle control is then administered interduodenally (i.d.) or subcutaneously (s.c.). Rats are housed 2/cage and sacrificed with $CO_2$ four hours after ligation. The stomachs are removed, rinsed, and contents emptied into a graduated centrifuge tube. The tubes are centrifuged for 20 minutes at 2,000 RPM and the volume of gastric juice recorded. Any samples obviously contaminated by feces, food, or hemolysis are eliminated. An aliquot of each is frozen for later analysis of $Na^+$, $K^+$, and $Cl^-$ concentration. The pH is measured and 1 ml. of gastric juice is titrated with 0.1 N NaOH to a pH of 7.0–7.4. The data are analyzed by either a Student's t-test or an analysis of variance depending upon which test is appropriate.

When administered according to this modified Shay et al. procedure in doses ranging from 1-100 mg/kg., the compounds of this invention, except 2-aminoiminomethylthio-3-quinoxalinecarboxylic acid ethyl ester, 2-[(imino(methylamino)methyl)thio]-3-quinoxalinecarboxylic acid ethyl ester and N-butylcarbamimidothioic acid-(3-methyl-2-quinoxalinyl)ester, exhibit significant anti-secretory properties.

The anti-secretory effects of compounds may be further determined using dog gastric secretory studies. In these studies unanesthetized dogs are prepared with either chronic gastric fistula, innervated gastric pouches or denervated gastric pouches as desired. The test compound is usually administered prior to stimulation intravenously, subcutaneously, intramuscularly, or orally in doses of 1–25 mg/kg. Where the compound is found to have an appetite-depressant effect, however, administration may be at the time of stimulation or at some interval following stimulation. Stimulation may generally be carried out using such stimulants as betazole hydrochloride, gastric tetrapeptide, 2-deoxy-glucose, or a food substance. The resulting gastric juices are collected and analyzed, inter alia, for volume, hydrogen ion, pepsin, and electrolytes.

Apart from effectiveness in reducing gastric ulcers and inhibiting gastric secretions as determined by the above-described testing procedures, a number of compounds of the invention are effective in lowering blood pressures as shown in standard tests using hypertensive rats. Such tests are conducted on spontaneously or surgically hypertensive rats. Test groups and control groups usually consist of 4–6 rats, and the test compounds and reference compounds are administered either orally or intraperitoneally. Systolic blood pressures are measured by an indirect technique using the Decker Caudal Plethysmorgraph or other appropriate sensor, and readings are taken prior to drug administration and periodically thereafter, for example at 1.5, 4 and 24 hours after administration. Results are analyzed statistically. Reference compounds used include clonidine, hydralazine, guanethidine, methyldopa and reserpine.

When administered in doses of 25–100 mg/kg. various compounds of the invention demonstrate weak to moderate abilities to reduce blood pressures. Those compounds of the invention which are moderately effective in lowering blood pressures are compounds of Formula I in which: A is methyl and Q, $R^1$, $R^2$, and $R^3$ are all hydrogen; A is methyl, Q and $R^2$ are hydrogen, and $R^1$ and $R^3$ are methyl; A is carbethoxy and Q, $R^1$, $R^2$, and $R^3$ are all hydrogen; A is carbethoxy, Q, $R^1$, and $R^2$ are hydrogen, and $R^3$ is methyl; A is carbethoxy, Q and $R^2$ are hydrogen, and $R^1$ and $R^3$ are both isopropyl; A is carbethoxy, Q and $R^2$ are hydrogen, and $R^1$ and $R^3$ are both butyl. A compound of the invention which is less effective in lowering blood pressures is the compound of Formula I in which A is carbethoxy, Q and $R^2$ are hydrogen, and $R^1$ and $R^3$ are ethyl. Additionally, the compound of Formula I in which A is methyl, Q is 6-nitro, and $R^1$, $R^2$, and $R^3$ are all hydrogen [carbamimidothioic acid (3-methyl-6-nitro-2-quinoxalinyl)ester] shows marked ability to reduce blood pressures when administered according to the described test procedure at a dose of 25 mg/kg. In contrast, the compound of Wolf et al., described above, in which Q, A, $R^1$, $R^2$, and $R^3$ of Formula I would all be hydrogen [carbamimidothioic acid(2-quinoxalinyl)ester] gave no affect on blood pressure when administered according to this procedure at doses of 75 mg/kg.

With respect to the anti-ulcer and anti-secretory properties of the compounds of the invention, the pharmacological mode of action of these compounds is not known. However, they do not appear to function as histamine ($H_2$) receptor antagonists, as is shown by the ineffectiveness of subject compounds in a screening procedure utilizing isolated guinea-pig atria. The test procedure used for these studies is that described by Black et al. in Nature, 236, 385-390 (1972), and is summarized as follows: Male guinea-pigs are killed by cervical dislocation and the thorax opened. The heart is removed and placed in oxygenated Krebs-Henseleit solution (NaCl-6.87, KCl 0.4, $MgSO_4.7H_2O$-0.14, $CaCl_2$-0.28, $NaH_2PO_4$-0.14, $NaHCO_3$-2.1, Glucose-2.0 g/l) at room temperature. The auricles are cut away from other tissue and ligatures are placed in the tips of each auricle. The organs are then placed in a 10 ml. organ bath, oxygenated with 95–5% $O_2$-$CO_2$, and attached to a Grass FT.03 force-displacement transducer. The atria are allowed to equilibrate for approximately 1 hr. before cumulative dose-response curves are determined for histamine. The test drug is then added to the bath and the tissue is again allowed to equilibrate for ½ hour. The histamine cumulative dose-response is then run in the presence of the drug. Standard compounds used for comparison are metiamide and histamine diphosphate. As stated above, when administered according to such procedure in 10 micromolar concentrations, several compounds of the invention exhibited no significant histamine $H_2$-receptor antagonist effect.

For pharmacological use, the compounds of Formula I may be administered in the form of an acid addition salt of a non-toxic organic or inorganic acid. Such salts may be prepared by methods well-known in the art. Appropriate salts may be formed from the following acids: hydrochloric, hydrobromic, sulfonic, sulfuric, phosphoric, nitric, methanesulfonic, and benzenesulfonic; of which the hydrochloric acid salts are preferred. Such salts are included in the scope of the invention.

When employed to reduce ulcers, to reduce gastric secretions, or to lower blood pressures, the effective dosage of the substance active for such treatment will vary according to the particular compound being employed, the severity and nature of condition being treated, and the particular subject being treated. Therapy should be initiated at lower doses (in mg/kg/day) in the effective ranges given above for the prescribed activity, the dosage thereafter being increased, if necessary, to produce the desired anti-ulcer, anti-secretory, or anti-hypertensive effect.

Further, when employed as anti-ulcer, anti-secretory, or anit-hypertensive agents, the compounds of the invention, or pharmacologically acceptable acid addition salts thereof, may be administered alone or in combination with pharmaceutically acceptable carriers. The proportion and nature of such carriers would be determined by the solubility and other chemical properties of the compound selected, the chosen route of administration, and standard pharmaceutical practice.

PREPARATION OF THE COMPOUNDS OF THE INVENTION

The novel compositions of matter of this invention are prepared by the following displacement reactions:

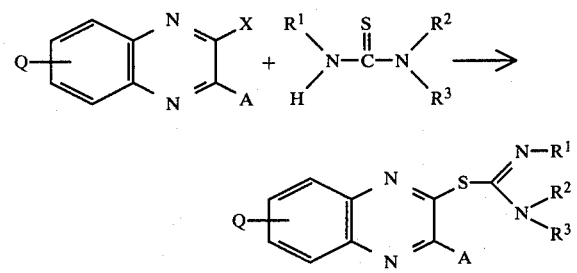

in which Q, A, $R^1$, $R^2$, and $R^3$ are set out above and X is halogen (preferrably chlorine). The reaction is run in an inert organic solvent, such as acetone or methanol, at temperatures ranging from room temperature to the reflux temperature of the solvent.

The following examples further illustrate the best mode of practicing this invention:

EXAMPLE 1

N,N'-Diethylcarbamimidothioic acid-(2-quinoxalinyl)ester, hydrochloride

2-Chloroquinoxaline (3.29 g., 0.02 mole) in 50 ml. of methanol was added to 2.65 g. (0.02 mole) of N-N'-diethyl thiourea in 25 ml. of methanol. The solution was stirred at room temperature under nitrogen for ¾ hour. The solvent was then evaporated and the residue was treated with ether which was again evaporated. The ether treatment was repeated several times. The residue was then covered with ether, treated with a little acetone and cooled. The solid which formed on standing was collected by filtration, washed, and dried. Recrystallization from methanol-ether gave 2.42 g. (40.7% yield) of product as a green solid, m.p. 91°–93° C.

Analysis for: $C_{13}H_{17}ClN_4S$ Calculated: C, 52.61; H, 5.77; N, 18.88; Cl, 11.94. Found: C, 52.24; H, 5.67; N, 18.91; Cl, 12.37.

EXAMPLE 2

Carbamimidothioic acid(3-methyl-2-quinoxalinyl)ester, hydrochloride

2-Chloro-3-methylquinoxaline (10.72 g., 0.06 mole) was dissolved in 150 ml. of acetone, treated with Norit and filtered. The filtrate was added to 4.56 g. (0.06 mole) of thiourea in 150 ml. acetone. The solution was stirred at reflux under nitrogen for 2 hours. The precipitate which began to form after 5 minutes, was filtered while the reaction mixture was hot. The solid was collected, washed with hot acetone and dried to give 11.85 g. of a pink solid, m.p. 156°–157° C.

Analysis for: $C_{10}H_{11}ClN_4S$ Calculated: C, 47.15; H, 4.35; N, 21.99; Cl, 13.92; S, 12.59. Found: C, 47.33; H, 4.37; N, 22.35; Cl, 13.96; S, 12.39.

A second crop gave an additional 1.66 g. (Total yield 88.4%).

EXAMPLE 3

N,N'-Dimethylcarbamimidothioic acid(3-methyl-2-quinoxalinyl)ester, hydrochloride 2-Chloro-3-methylquinoxaline (3.572 g., 0.02 mole) was dissolved in 17 ml. of methanol, treated with Norit and filtered. The filtrate was added to 2.084 g. (0.02 mole) N,N'-dimethylthiourea dissolved in 25 ml. of methanol. The solution was stirred at reflux for 4 hours, cooled, and evaporated to a solid residue. The residue was triturated successively with ether and acetone, filtered and dried to give 3.554 g., 62.8% of product, m.p. 130°–131.5°.

Analysis for: $C_{12}H_{15}ClN_4S$ Calculated: C, 50.97; H, 5.35; N, 19.81; Cl, 12.54; S, 11.34. Found: C, 50.64; H, 5.22; N, 19.74; Cl, 12.52; S, 11.18.

EXAMPLE 4

N,N'-Diethylcarbamimidothioic acid(3-methyl-2-quinoxalinyl)ester, hydrochloride

2-Chloro-3-methylquinoxaline (15.0 g., 0.084 mole) was dissolved in 225 ml. of acetone, treated with Norit and filtered. The filtrate was added to 11.11 g. (0.084 mole) of 1,3-diethylthiourea in 175 ml. of acetone and the mixture was stirred at room temperature for 5½ hours. The solid which separated was filtered and washed well with acetone, then with ether and dried to give 18.12 g. (69.7%) of product, m.p. 121.5°–122°.

Analysis for: $C_{14}H_{19}ClN_4S$

Calculated: C, 54.10; H, 6.16; N, 18.02; Cl, 11.40. Found: C, 54.06; H, 6.12; N, 18.29; Cl, 11.39.

EXAMPLE 5

N,N'-Dibutylcarbamimidothioic acid(3-methyl-2-quinoxalinyl)ester, hydrochloride

2-Chloro-3-methylquinoxaline (3.572 g., 0.02 mole) was dissolved in 50 ml. of methanol, treated with Norit and filtered. The filtrate was added to 3.767 g. (0.02 mole) of 1,3-dibutylthiourea dissolved in 25 ml. of methanol. The resulting solution was stirred at room temperature for 1 hour and evaporated on a rotary evaporator. The residual oil was triturated successively with several portions of ether, 2:1 pentane-ether and acetone, and was filtered and washed with pentane, to give 2.60 g. (38.6%) of product as a tan solid, m.p. 97°–99°.

Analysis for: $C_{18}H_{27}ClN_4S$ Calculated: C, 58.92; H, 7.41; N, 15.27; Cl, 9.66; S, 8.74. Found: C, 58.93; H, 7.50; N, 15.31; Cl, 9.71; S, 9.01.

EXAMPLE 6

N-Butylcarbamimidothioic acid(3-methyl-2-quinoxalinyl)ester, hydrochloride

2-Chloro-3-methylquinoxaline (3.572 g., 0.02 mole) was dissolved in 50 ml. of acetone treated with Norit and filtered. The filtrate was added to a solution of 2.645 g. (0.02 mole) n-butylthiourea in 25 ml. acetone. After the mixture was stirred at room temperature for 3½ hours, the solid which had formed was filtered, washed with acetone, then ether and dried to give 4.86 g. (78.2%) of product as an off-white solid, m.p. 118.5°–119.5°.

Analysis for: $C_{14}H_{19}ClN_4S$ Calculated: C, 54.10; H, 6.16; N, 18.02; Cl, 11.40. Found: C, 54.05; H, 6.15; N, 18.17; Cl, 11.41.

Note: This compound may exist as the N'-butyl tautomer or a mixture of the two tautomers, although the analytical data point to the presence of the named compound.

EXAMPLE 7

N-(2-Propenyl)carbamimidothioic acid(3-methyl-2-quinoxalinyl)ester, hydrochloride 2-Chloro-3-methylquinoxaline (5.359 g., 0.03 mole) was dissolved in 75 ml. of acetone, treated with Norit and filtered. The filtrate was added to a solution of 3.485 g. (0.03 mole) of allylthiourea in 50 ml. of acetone while the solution was stirred at room temperature under $N_2$. A precipitate had formed at the end of 2 hours. Stirring was continued for 3½ hours. The solid that was filtered off was washed with acetone, then ether and dried, to give 6.68 g. (75.6% yield) of product as a pink solid, m.p. 113°–114° C.

Analysis for: $C_{13}H_{15}ClN_4S$ Calculated: C, 52.97; H, 5.13; N, 19.01; Cl, 12.02; S, 10.87. Found: C, 52.78; H, 5.09; N, 19.33; Cl, 12.05; S, 10.77.

Note: The analytical data were not conclusive as to whether this product as the named compound or the N'-(2-propenyl) tautomer or a mixture of the two tautomers.

EXAMPLE 8

N,N'-Bis(2-propenyl)carbamimidothioic acid(3-methyl-2-quinoxalinyl)ester, hydrochloride 2-Chloro-3-methylquinoxaline (3.56 g., 0.02 mole) was dissolved in 50 ml. of methanol, treated with Norit and filtered. The filtrate was added to 3.125 g. (0.02 mole) of 1,3-diallylthiourea in 50 ml. of methanol. The mixture was stirred at room temperature for 3½ hours, then freed of solvent. Acetone was added to the residue and the solution again freed of solvent. The residue was triturated with ether and with acetone, filtered, washed and dried to give 4.12 g. (61.5% yield), m.p. 90°–93° C.

Analysis for: $C_{16}H_{19}ClN_4S$ Calculated: C, 57.39; H, 5.72; N, 16.73; Cl, 10.59. Found: C, 56.99; H, 5.66; N, 16.58; Cl, 10.77.

EXAMPLE 9

3-Methyl-2-(4,5,6,7-tetrahydro-1H-1,3-diazepin-2-ylthio)-quinoxaline, hydrochloride 2-Chloro-3-methylquinoxaline (5.36 g., 0.03 mole) was dissolved in 150 ml. methanol, treated with Norit and filtered. The filtrate was added to 3.91 g. (0.03 mole) of tetrahydro-1,3-diazepine-2-thione. The mixture was stirred in a waterbath heated at 50° C. for 2 hours. The resulting orange solution was concentrated to a volume of 75 ml., then diluted with 150 ml. acetone. The mixture was chilled and 2.5 g. of a solid collected. An additional 3.2 g. of solid was recovered from the mother liquor. The two solids were combined and recrystallized from methanolacetone to give the product as 1.15 g. (12.4%), white solid, m.p. 170°–173° C. (dec)

Analysis for: $C_{14}H_{17}ClN_4S$ Calculated: C, 54.45; H, 5.55; N, 18.14; Cl, 11.48. Found: C, 54.42; H, 5.46; N, 18.17; Cl, 11.52.

EXAMPLE 10

2-(Aminoiminomethylthio)-3-quinoxalinecarboxylic acid ethyl ester, hydrochloride 2-Chloro-3-quinoxalinecarboxylic acid ethyl ester (9.5 g., 0.04 mole) and 3.052 g. (0.04 mole) of thiourea were dissolved in 200 ml. of acetone. The solution was boiled in an open flask for 1½ hours during which acetone was added to maintain the volume at 200 ml. The reaction mixture was cooled and the solid was collected by filtration to give 7.8 g. of crude product. Recrystallization from methanol-acetone afforded 3.55 g. of off-white solid, over wide range dec.

Analysis for: $C_{12}H_{13}ClN_4O_2S$ Calculated: C, 46.08; H, 4.19; N, 17.91; Cl, 11.33; S, 10.25. Found: C, 46.01; H, 4.13; N, 17.85; Cl, 11.38; S, 10.32.

An additional 4.05 g. of product was recovered from the reaction mixture to give a total yield of 7.60 g. (59.3%). Found: C, 46.06; H, 4.14; N, 17.79; Cl, 11.38; S, 10.37

EXAMPLE 11

2-[(Amino(methylimino)methyl)thio]-3-quinoxalinecarboxylic acid ethyl ester, hydrochloride or 2-[(Imino(methylamino)methyl)thio]-3-quinoxalinecarboxylic acid ethyl ester, hydrochloride 2-Chloro-3-quinoxalinecarboxylic acid ethyl ester (4.733 g., 0.02 mole) and 1.803 g. (0.02 mole) of monomethylthiourea were dissolved in 100 ml. of acetone and the solution as stirred at reflux for 1½ hours, cooled, and filtered to give 5.62 g. of crude solid. Extraction of the crude solid with boiling acetonitrile left 3.14 g. of insoluble product, m.p. 180° (dec.).

Analysis for: $C_{13}H_{15}ClN_4O_2S$ Calculated: C, 47.78; H, 4.63; N, 17.14; Cl, 10.85; S, 9.81. Found: C, 47.65; H, 4.73; N, 17.03; Cl, 10.83; S, 9.99.

An additional amount of product was recovered from the filtrate to give a total yield of 4.94 g. (75.6%).

Note: The analytical data were not conclusive as to whether the product was one or the other of the named tautomers or a mixture of the two tautomers.

EXAMPLE 12

2-[(Methylamino(methylamino)methylthio]-3-quinoxalinecarboxylic acid ethyl ester, hydrochloride 2-Chloro-3-quinoxalinecarboxylic acid, ethyl ester (4.733 g., 0.02 mole) and 2.084 g., (0.02 mole) of N,N'- dimethylthiourea were dissolved in a solution of 10 ml. of acetic acid and 90 ml. of acetone. The mixture was heated at reflux for 1 hour, cooled in an icebath and filtered. The residue was washed with acetone, triturated with two portions of acetonitrile, washed with ether, and dried to give 4.70 g. of the product, m.p. 162°–163.5° (dec.)

Analysis for: $C_{14}H_{17}ClN_4O_2S$ Calculated: C, 49.34; H, 5.03; N, 16.44; Cl, 10.40; S, 9.41. Found: C, 49.51; H, 5.06; N, 16.39; Cl, 10.48; S, 9.74.

An additional 0.961 g. product (m.p. 161°–162° C. dec.) was recovered from the mother liquor to give a total yield of 5.66 g. (83%).

EXAMPLE 13

2-[Ethylamino(ethylimino)methylthio]-3-quinoxalinecarboxylic acid ethyl ester, hydrochloride 2-Chloro-3-quinoxalinecarboxylic acid, ethyl ester (7.100 g., 0.03 mole) and 3.967 g., (0.03 mole) of 1,3-diethylthiourea were dissolved in 150 ml. of acetone and boiled in an open flask for 1 hour. The reaction mixture was stirred at room temperature for 1 hour, then concentrated to a volume of 50 ml. After standing at room temperature overnight, the mixture was filtered and the solid residue washed with acetone and ether. Recrystallized from a mixture of methanol, acetone and ether it gave 7.182 g. product, m.p. 144.5°–145° C.

An additional 1.575 g. of product (m.p. 145°–146°) was recovered from the mother liquor to give a total yield of 8.76 g. (79.1%).

Analysis for: $C_{16}H_{21}ClN_4O_2S$ Calculated: C, 52.10; H, 5.74; N, 15.19; Cl, 9.61; S, 8.69. Found: C, 51.93; H, 5.52; N, 15.11; Cl, 9.93; S, 8.73.

EXAMPLE 14

2-[(1-Methylethylamino)(1-methylethylimino)methylthio]-3-quinoxalinecarboxylic acid ethyl ester, hydrochloride 2-Chloro-3-quinoxalinecarboxylic acid ethyl ester (4.73 g., 0.02 mole) and 3.206 g. (0.02 mole) of 1,3-diisopropylthiourea were dissolved in 90 ml. of acetone and 10 ml. of acetic acid. The solution was heated on the steambath for 2¾ hours and filtered hot. The solvent in the filtrate was evaporated and the residue was triturated with ether until it solidified. Filtration gave 2.33 g. of crude product. Recrystallized from acetone-ether it afforded 1.28 g. (16.1%) of a yellow solid, m.p. 148°–149° C. (dec).

Analysis for: $C_{18}H_{25}ClN_4O_2S$ Calculated: C, 54.47; H, 6.35; N, 14.12; Cl, 8.93; S, 8.08. Found: C, 54.44; H, 6.18; N, 14.19; Cl, 8.96; S, 8.25.

In second preparation the heating period was shortened to 1½ hours and the product melting at 146°–148° C. was obtained in 58.3% yield.

EXAMPLE 15

2-[(Propylamino)(propylimino)methylthio]-3-quinoxalinecarboxylic acid ethyl ester, hydrochloride 2-Chloro-3-quinoxalinecarboxylic acid ethyl ester (3.551 g., 0.015 mole) and 2.405 g. (0.015 mole) of 1,3-di-n-propylthiourea were dissolved in acetone and heated at reflux for 1½ hours. The solution was concentrated to a volume of 50 ml. and cooled. A small amount of solid was removed by filtration. The filtrate was further concentrated to a volume of 25 ml. and ether was added to turbidity. After the reaction mixture had been cooled the yellow solid was collected by filtration to give 2.77 g. (46.6%) of the product, m.p. 129°–130° C.

Analysis for: $C_{18}H_{25}ClN_4O_2S$ Calculated: C, 54.47; H, 6.35; N, 14.12; Cl, 8.93; S, 8.08. Found: C, 54.42; H, 6.50; N, 14.12; Cl, 8.87; S, 8.07.

EXAMPLE 16

2-[(Butylamino)(butylimino)methylthio]-3-quinoxalinecarboxylic acid ethyl ester, hydrochloride 2-Chloro-3-quinoxalinecarboxylic acid ethyl ester (7.10 g., 0.03 mole) was dissolved in 125 ml. of acetone treated with Norit and filtered. The filtrate was added to 5.650 g. (0.03 mole) of 1,3-di-n-butylthiourea in 100 ml. of acetone. The solution was stirred at reflux under a nitrogen atmosphere for 6 hours, allowed to cool to room temperature, and stirred an additional 17 hours. The red solution was treated with Norit, filtered, and concentrated to a volume of 100 ml. The yellow solid that crystallized out was collected by filtration, washed and dried to give the 6.05 g. (47.5% yield) of product, m.p. 138°–139° C. (dec.).

Analysis for: $C_{20}H_{29}ClN_4O_2S$ Calculated: C, 56.52; H, 6.88; N, 13.18; Cl, 8.34. Found: C, 56.74; H, 6.78; N, 13.25; Cl, 8.09.

EXAMPLE 17

Carbamimidothioic acid(3-methyl-6-nitro-2-quinoxalinyl)ester, hydrochloride

2-Chloro-3-methyl-6-nitroquinoxaline (5.59 g., 0.025 mole) in 400 ml. of acetone was added to 1.91 g. (0.025 mole) of thiourea in 100 ml. of acetone. The mixture was stirred at room temperature under nitrogen for 4½ hours. The red solid that formed was collected by filtration, washed with acetone and dried to give the 3.91 g. of product, m.p. 156.5°–157° C. (dec.).

Analysis for: $C_{10}H_{10}ClN_5O_2S \cdot \tfrac{1}{4}H_2O$ Calculated: C, 39.48; H, 3.48; N, 23.03; Cl, 11.65; S, 10.54. Found: C, 39.45; H, 3.42; N, 22.74; Cl, 11.30; S, 10.22.

A second crop 1.48 g. of product, (m.p. 151°–152° C. dec.) was recovered from the mother liquor, bringing the total yield to 71.8%.

What is claimed is:

1. A compound of the formula:

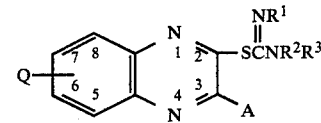

in which

Q is hydrogen or nitro;

A is hydrogen, methyl, ethyl, propyl, isopropyl, n-butyl, carbomethoxy, carbethoxy, carbopropoxy, carbisopropoxy, carbobutoxy, carbisobutyoxy, or carbo-t-butoxy; and $R^1$ and $R^2$ are, independently, hydrogen, methyl, ethyl, propyl, isopropyl, n-butyl, isobutyl, t-butyl, allyl, or $R^1$ and $R^2$ may be concatenated with a 1,4-hydrocarbylene or 1,4-hydrocarbenylene chain of 4 carbon atoms; except that, when A and Q are hydrogen, $R^1$ and $R^2$ may not both be hydrogen; and with the further exception that, where A is methyl and $R^1$ and Q are both hydrogen, $R^2$ may not be ethyl;

or a pharmaceutically acceptable salt thereof.

2. A compound as defined in claim 1 in which Q is hydrogen.

3. A compound as defined in claim 2 in which A is methyl, ethyl, propyl, isopropyl, or n-butyl.

4. A compound as defined in claim 2 in which A is carbomethoxy, carbethoxy, carbopropoxy, carboisopropoxy, carbobutoxy, carboisobutoxy, or carbo-t-butoxy.

5. A compound as defined in claim 2 which is N,N'-diethylcarbamimdothioic acid(2-quinoxalinyl)ester or a pharmaceutically acceptable salt thereof.

6. A compound as defined in claim 3 which is carbamimidothioic acid(3-methyl-2-quinoxalinyl)ester or a pharmaceutically acceptable salt thereof.

7. A compound as defined in claim 3 which is N,N'-dimethylcarbamimidothioic acid(3-methyl-2-quinoxalinyl)ester or a pharmaceutically acceptable salt thereof.

8. A compound as defined in claim 3 which is N,N'-diethylcarbamimidothoic acid(3-methyl-2-quinoxalinyl)ester or a pharmaceutically acceptable salt thereof.

9. A compound as defined in claim 3 which is N,N'-dibutylcarbamimidothioic acid(3-methyl-2-quinoxalinyl)ester or a pharmaceutically acceptable salt thereof.

10. A compound as defined in claim 3 which is N-butylcarbamimidothioic acid(3-methyl-2-quinoxalinyl)ester or a pharmaceutically acceptable salt thereof.

11. A compound of claim 3 in which at least one of $R^1$ $R^2$ is allyl or $R^1$ and $R^2$ are concatenated with a 1,4-hydrocarbylene or 1,4-hydrocarbenylene chain of 4 carbon atoms.

12. A compound as defined in claim 11 which is N-(2-propenyl)carbamimidothioic acid(3-methyl-2-quinoxalinyl)ester or a pharmaceutically acceptable salt thereof.

13. A compound as defined in claim 11 which is N,N'-bis-(2-propenyl)carbamimidothioic acid(3-methyl-2-quinoxalinyl)ester or a pharmaceutically acceptable salt thereof.

14. A compound as defined in claim 11 which is 3-methyl-2-(4,5,6,7-tetrahydro-1H-1,3-diazepin-2-ylthio)-quinoxaline or a pharmaceutically acceptable salt thereof.

15. A compound as defined in claim 4 which is 2-(aminoiminomethylthio)-3-quinoxalinecarboxylic acid ethyl ester or a pharmaceutically acceptable salt thereof.

16. A compound as defined in claim 4 which is 2-[(imino(methylamino)methyl)thio]-3-quinoxalinecarboxylic acid ethyl ester or a pharmaceutically acceptable salt thereof.

17. A compound as defined in claim 4 which is 2-[(methylamino)(methylimino)methylthio]-3-quinoxalinecarboxylic acid ethyl ester or a pharmaceutically acceptable salt thereof.

18. A compound as defined in claim 4 which is 2-[ethylamino(ethylimino)methylthio]-3-quinoxalinecarboxylic acid ethyl ester or a pharmaceutically acceptable salt thereof.

19. A compound as defined in claim 4 which is 2-[(1-isopropylamino)-1-isopropylimino)methylthio]-3-quinoxalinecarboxylic acid ethyl ester or a pharmaceutically acceptable salt thereof.

20. A compound as defined in claim 4 which is 2-[(propylamino)(propylimino)methylthio]-3-quinoxalinecarboxylic acid ethyl ester or a pharmaceutically acceptable salt thereof.

21. A compound as defined in claim 4 which is 2-[(butylamino)(butylimino)methylthio]-3-quinoxalinecarboxylic acid ethyl ester or a pharmaceutically acceptable salt thereof.

22. A compound of claim 1 in which Q is 6-nitro.

23. A compound as defined in claim 22 which is carbamimidothioic acid(3-methyl-6-nitro-2-quinoxalinyl)ester or a pharmaceutically acceptable salt thereof.

* * * * *